(12) United States Patent
Fukuchi et al.

(10) Patent No.: US 11,192,836 B2
(45) Date of Patent: Dec. 7, 2021

(54) METHOD AND APPARATUS FOR PRODUCING FLUORINE-CONTAINING ORGANIC COMPOUND

(71) Applicant: SHOWA DENKO K.K., Tokyo (JP)

(72) Inventors: Yohsuke Fukuchi, Tokyo (JP); Shinichi Yorozuya, Tokyo (JP); Nozomi Kusumoto, Tokyo (JP); Hiroshi Kobayashi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 16/770,115

(22) PCT Filed: Nov. 7, 2018

(86) PCT No.: PCT/JP2018/041370
§ 371 (c)(1),
(2) Date: Jun. 5, 2020

(87) PCT Pub. No.: WO2019/116789
PCT Pub. Date: Jun. 20, 2019

(65) Prior Publication Data
US 2020/0346998 A1    Nov. 5, 2020

(30) Foreign Application Priority Data
Dec. 12, 2017    (JP) .............................. JP2017-237871

(51) Int. Cl.
*C07C 17/10*    (2006.01)
*B01J 4/02*    (2006.01)
*B01J 10/00*    (2006.01)
(Continued)

(52) U.S. Cl.
CPC ................. *C07C 17/10* (2013.01); *B01J 4/02* (2013.01); *B01J 10/00* (2013.01); *B01J 19/0006* (2013.01);
(Continued)

(58) Field of Classification Search
CPC ....... C07C 17/10; C07C 19/10; C07C 67/287; C07C 69/76; C07C 67/307; C07C 69/75;
(Continued)

(56) References Cited

U.S. PATENT DOCUMENTS

| 4,377,715 A | 3/1983 | Nychka et al. |
| 5,753,776 A | 5/1998 | Bierschenk et al. |

(Continued)

FOREIGN PATENT DOCUMENTS

| JP | 4-500520 A | 1/1992 |
| JP | 2001-311686 A | 11/2001 |

(Continued)

OTHER PUBLICATIONS

Tetrafluoromethane, p. 3, published Feb. 2017 (Year: 2017).*
(Continued)

*Primary Examiner* — Yevgeny Valenrod
*Assistant Examiner* — Blaine G Doletski
(74) *Attorney, Agent, or Firm* — Sughrue Mion, PLLC

(57) ABSTRACT

Provided is a method for producing a fluorine-containing organic compound. The method can immediately detect the occurrence of a side reaction in direct fluorination reaction using fluorine gas and can give a highly pure fluorine-containing organic compound at a high yield. A raw material liquid (1) containing a raw material organic compound having a hydrogen atom and two or more carbon atoms is reacted with fluorine gas in a reaction container (11) to replace the hydrogen atom of the raw material organic compound with a fluorine atom to give a fluorine-containing organic compound. In the reaction, tetrafluoromethane contained in a gas phase (2) in the reaction container (11) is continuously measured, and the amount of the fluorine gas supplied to the reaction container (11) is controlled depending on the measured value of the tetrafluoromethane.

4 Claims, 1 Drawing Sheet

(51) Int. Cl.
*B01J 19/00* (2006.01)
*C07C 67/287* (2006.01)
(52) U.S. Cl.
CPC ... *C07C 67/287* (2013.01); *B01J 2219/00186* (2013.01)
(58) Field of Classification Search
CPC . B01J 4/02; B01J 10/00; B01J 19/0006; B01J 2219/00186; B01J 12/00; B01J 2204/002; B01J 2219/00164; B01J 4/002; B01J 4/008
See application file for complete search history.

(56) References Cited

U.S. PATENT DOCUMENTS

| | | | | |
|---|---|---|---|---|
| 2002/0051132 | A1* | 5/2002 | Ohno | G01N 33/0052 356/437 |
| 2003/0157800 | A1 | 8/2003 | Ohno et al. | |
| 2007/0155996 | A1* | 7/2007 | Luly | C07B 39/00 570/123 |
| 2011/0112341 | A1 | 5/2011 | Ohno et al. | |

FOREIGN PATENT DOCUMENTS

| | | |
|---|---|---|
| JP | 2002-069014 A | 3/2002 |
| WO | 2010/001774 A1 | 1/2010 |

OTHER PUBLICATIONS

International search report in English for PCT/JP2018/041370 dated Dec. 18, 2018.
International Preliminary Report on Patentability dated Jun. 16, 2020 from the International Bureau in International Application No. PCT/JP2018/041370.

* cited by examiner

METHOD AND APPARATUS FOR PRODUCING FLUORINE-CONTAINING ORGANIC COMPOUND

CROSS-REFERENCE TO RELATED APPLICATIONS

This application is a National Stage of International Application No. PCT/JP2018/041370 filed on Nov. 7, 2018, which claims priority under U.S.C. § 119(a) to Japanese Patent Application No. 2017-237871 filed on Dec. 12, 2017.

TECHNICAL FIELD

The present invention relates to a method and an apparatus for producing a fluorine-containing organic compound.

BACKGROUND ART

A direct fluorination reaction in which an organic compound is reacted with fluorine gas to replace hydrogen atoms of the organic compound with fluorine atoms to give a fluorine-containing organic compound is known. This direct fluorination reaction is an exothermic reaction generating a large amount of reaction heat, which increases the temperature of a reaction field to be likely to cause side reactions. When a side reaction is caused, the yield or the purity of a fluorine-containing organic compound as the target compound may decrease.

For example, PTL 1 discloses a method of giving a target compound at a high yield by a direct fluorination reaction with a porous tubular reaction container while side reactions are suppressed. PLT 2 discloses a method of giving highly pure octafluoropropane by a direct fluorination reaction while the formation of impurities difficult to separate are suppressed.

CITATION LIST

Patent Literature

PTL 1: U.S. Pat. No. 4,377,715 B
PTL 2: JP 2002-69014 A

SUMMARY OF INVENTION

Technical Problem

Fluorine gas reacts vigorously, and thus it is not easy to completely suppress side reactions in the direct fluorination reaction unfortunately. In addition, glass has insufficient corrosion resistance against fluorine gas, thus a transparent material such as glass cannot be used as the material of a reaction container for the direct fluorination reaction, and an opaque metal is typically used. On this account, the contents of a reaction container cannot be visually monitored, thus it is difficult to immediately find the occurrence of a side reaction, and the formation of impurities is not easily suppressed sufficiently.

A reaction solution can be sampled from a reaction container during reaction to detect the occurrence of a side reaction, but fluorine gas has extremely high reactivity and may instantly cause a side reaction. Hence, a method of occasionally sampling a reaction solution to be analyzed is difficult to immediately detect the occurrence of a side reaction.

The present invention is intended to provide a method and an apparatus for producing a fluorine-containing organic compound, and the method and the apparatus can immediately detect the occurrence of a side reaction in a direct fluorination reaction using fluorine gas and can give a highly pure fluorine-containing organic compound at a high yield.

Solution to Problem

To solve the problems, aspects of the present invention are the following [1] to [9].

[1] A method for producing a fluorine-containing organic compound, the method including reacting a raw material liquid containing a raw material organic compound having a hydrogen atom and two or more carbon atoms with fluorine gas in a reaction container to replace the hydrogen atom of the raw material organic compound with a fluorine atom to give a fluorine-containing organic compound, in which tetrafluoromethane contained in a gas phase in the reaction container is continuously measured, and the amount of the fluorine gas supplied to the reaction container is controlled depending on the measured value of the tetrafluoromethane.

[2] The method for producing a fluorine-containing organic compound according to the aspect [1], in which the gas phase in the reaction container is introduced to an infrared spectrometer to measure the tetrafluoromethane.

[3] The method for producing a fluorine-containing organic compound according to the aspect [2], in which the infrared spectrometer is used to measure peaks around wavelengths of 798 cm$^{-1}$, 1240 cm$^{-1}$, 1290 cm$^{-1}$, 1540 cm$^{-1}$, and 2200 cm$^{-1}$.

[4] The method for producing a fluorine-containing organic compound according to the aspect [2], in which when the peak around a wavelength of 1290 cm$^{-1}$ measured with the infrared spectrometer has an intensity exceeding a predetermined intensity, the amount of the fluorine gas supplied is reduced, or the supply of the fluorine gas is stopped.

[5] The method for producing a fluorine-containing organic compound according to any one of the aspects [1] to [4], in which the fluorine-containing organic compound has a chemical structure in which all hydrogen atoms of the raw material organic compound are replaced with fluorine atoms.

[6] The method for producing a fluorine-containing organic compound according to any one of the aspects [1] to [4], in which the raw material organic compound is 1,2,3,4-tetrachlorobutane, and the fluorine-containing organic compound is 1,2,3,4-tetrachloro-1,1,2,3,4,4-hexafluorobutane.

[7] An apparatus for producing a fluorine-containing organic compound, the apparatus including a reaction container in which a raw material liquid containing a raw material organic compound having a hydrogen atom and two or more carbon atoms is reacted with fluorine gas to replace the hydrogen atom of the raw material organic compound with a fluorine atom to give a fluorine-containing organic compound, and a pipe through which a gas phase in the reaction container is introduced to an infrared spectrometer.

[8] The apparatus for producing a fluorine-containing organic compound according to the aspect [7], in which the fluorine-containing organic compound has a chemical structure in which all hydrogen atoms of the raw material organic compound are replaced with fluorine atoms.

[9] The apparatus for producing a fluorine-containing organic compound according to the aspect [7], in which the raw material organic compound is 1,2,3,4-tetrachlorobutane, and the fluorine-containing organic compound is 1,2,3,4-tetrachloro-1,1,2,3,4,4-hexafluorobutane.

Advantageous Effects of Invention

According to the present invention, the occurrence of a side reaction can be immediately detected in the direct fluorination reaction using fluorine gas, and a highly pure fluorine-containing organic compound can be produced at a high yield.

DESCRIPTION OF EMBODIMENTS

An embodiment of the present invention will now be described. The present embodiment is merely an example of the present invention, and the present invention is not limited to the present embodiment. Various modifications or improvements can be made in the present embodiment, and such various modifications and improvements can be encompassed by the present invention.

A method for producing a fluorine-containing organic compound pertaining to the present embodiment includes reacting a raw material liquid containing a raw material organic compound having a hydrogen atom and two or more carbon atoms with fluorine gas ($F_2$) in a reaction container to replace the hydrogen atom of the raw material organic compound with a fluorine atom to give a fluorine-containing organic compound. In the method, tetrafluoromethane ($CF_4$) contained in a gas phase in the reaction container is continuously measured, and the amount of the fluorine gas supplied to the reaction container is controlled depending on the measured value of the tetrafluoromethane.

With such a structure, tetrafluoromethane as a product of a side reaction in a direct fluorination reaction using fluorine gas can be detected immediately after the formation, and thus the occurrence of a side reaction of the direct fluorination reaction can be immediately detected. According to the method for producing a fluorine-containing organic compound pertaining to the present embodiment, the occurrence of a side reaction can be suppressed to sufficiently suppress the formation of impurities, and thus a fluorine-containing organic compound widely used in the semiconductor field, the medical and agrochemical field, general fields, and other fields can be produced at a high purity and a high yield. In addition, even when a reaction container is made from an opaque material, and the contents in the reaction container cannot be visually monitored, the occurrence of a side reaction of the direct fluorination reaction can be immediately detected.

Figure 1:
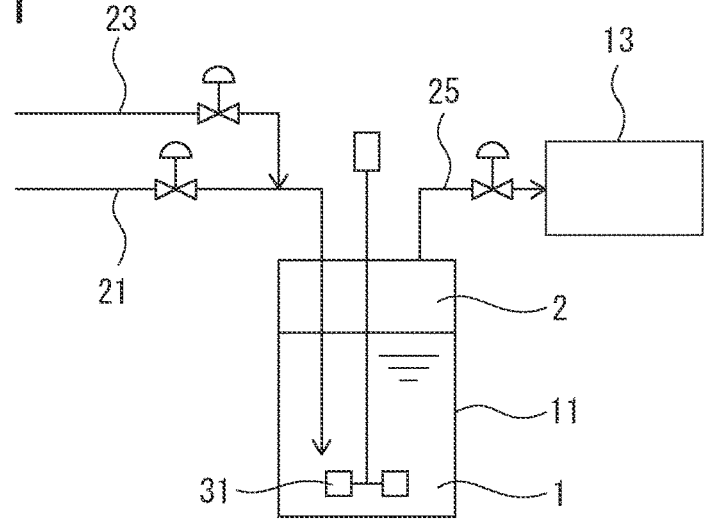
FIG. 1 is a schematic view illustrating a structure of an embodiment of an apparatus for producing a fluorine-containing organic compound pertaining to the present invention.

Examples of the apparatus for conducting such a method for producing a fluorine-containing organic compound pertaining to the present embodiment as described above include an apparatus for producing a fluorine-containing organic compound illustrated in FIG. 1. The apparatus for producing a fluorine-containing organic compound in FIG. 1 includes a reaction container 11 in which a raw material liquid 1 containing a raw material organic compound having a hydrogen atom and two or more carbon atoms is reacted with fluorine gas to replace the hydrogen atom of the raw material organic compound with a fluorine atom to give a fluorine-containing organic compound, a fluorine gas introduction pipe 21 through which fluorine gas is introduced into the reaction container 11, and a gas discharge pipe 25 through which a gas phase 2 in the reaction container 11 is introduced to an infrared spectrometer 13.

The reaction container 11 is made, for example, from a metal such as stainless steel and is to store the raw material liquid 1. To a point midway of the fluorine gas introduction pipe 21, a dilution gas pipe 23 is connected. Through the dilution gas pipe 23, a dilution gas is introduced to the fluorine gas introduction pipe 21, and the fluorine gas and the dilution gas can be mixed in the fluorine gas introduction pipe 21 to give a mixed gas in which the fluorine gas is diluted with the dilution gas.

An outlet at an end (an end at the downstream side) of the fluorine gas introduction pipe 21 is placed at a bottom part in the reaction container 11 and is to supply fluorine gas or a mixed gas to the bottom part in the reaction container 11.

An end at the upstream side of the gas discharge pipe 25 is connected to a top part of the reaction container 11, whereas an end at the downstream side is connected to a gas cell of the infrared spectrometer 13, and this structure enables introduction of the gas phase 2 in the reaction container 11 to the gas cell of the infrared spectrometer 13.

The side reaction in the present invention means "burning" of a raw material organic compound by reaction with fluorine gas. Although typical burning means that an organic compound and oxygen are continuously reacted with heat generation to turn into carbon dioxide and water, the "burning" of a raw material organic compound by reaction with fluorine gas means that a raw material organic compound and fluorine gas are continuously reacted with heat generation, as with the case of oxygen.

In the "burning" with fluorine gas, even carbon-carbon bonds of a raw material organic compound are cut by vigorous reaction and resulting heat generation. In other words, the side reaction in the present invention means the occurrence of reactions that include cutting of carbon-carbon bonds of a raw material organic compound by the "burning" with fluorine gas and are often caused when a raw material organic compound and fluorine gas are reacted to give a fluorine-containing organic compound.

The generation mechanism of the "burning" with fluorine gas will be explained as follows: The reaction heat of the reaction between fluorine gas and a raw material organic compound gradually increases the temperature at an outlet through which fluorine gas is blown into a raw material liquid containing the raw material organic compound. If the reaction heat can be removed, the reaction proceeds successfully, but if a high-temperature portion is locally generated and the high-temperature portion has a certain temperature or higher, "burning" with fluorine gas starts.

Once the "burning" starts, the burning continues unless the supply of fluorine gas is stopped, and thus to stop the "burning", the generation of reaction heat at the outlet of fluorine gas is required to be stopped. In other words, stopping the supply of fluorine gas enables stopping the "burning". When the "burning" can be stopped, the loss of a raw material organic compound by the "burning" can be suppressed. As described above, by monitoring "burning" to control the occurrence thereof, the purity and the yield of a fluorine-containing organic compound as the target compound can be improved.

When the "burning" occurs, various fluorine compounds such as hydrogen fluoride are formed. The present invention focuses on tetrafluoromethane of the various fluorine compounds. The formation of tetrafluoromethane is continuously monitored, and the amount of the fluorine gas supplied is controlled depending on the measured value of the tetrafluoromethane. For example, immediately after detection of the formation of tetrafluoromethane, a control is performed such that the amount of the fluorine gas supplied is reduced or the supply of the fluorine gas is stopped. By such a control, the loss of a raw material organic compound by "burning" can be simply suppressed. In other words, when a reaction is performed while reaction conditions are controlled and no formation of tetrafluoromethane is observed, the "burning" can be suppressed, and a fluorine-containing organic compound as the target compound can be produced at a high purity and a high yield.

In the present embodiment, the direct fluorination reaction is performed in a liquid phase. Hence, the raw material liquid containing a raw material organic compound is required to be liquid in a reaction condition for the direct fluorination reaction. When a raw material organic compound is liquid in a reaction condition for the direct fluorination reaction, the raw material organic compound can be used as it is as the raw material liquid, or a raw material organic compound solution in which the raw material organic compound is dissolved in a solvent that is not vigorously reacted with fluorine gas (for example, perfluorocarbon, carbon tetrachloride, or 1,2,3,4-tetrachloro-1,1,2,3,4,4-hexafluorobutane) can be used as the raw material liquid. When a raw material organic compound is solid or gas in a reaction condition for the direct fluorination reaction, a raw material organic compound solution in which the raw material organic compound is dissolved in a solvent that is not vigorously reacted with fluorine gas is used as the raw material liquid.

The raw material organic compound has at least one hydrogen atom in the structure thereof. The hydrogen atom is replaced by the reaction with fluorine gas, and accordingly the raw material organic compound is converted into a fluorine-containing organic compound. The replacement reaction of hydrogen atoms with fluorine atoms generates a large amount of heat, and thus the control of "burning" is important.

The raw material organic compound is an organic compound having two or more carbon atoms. When a compound has one carbon atom, a target product formed by the reaction with fluorine gas is not distinguished from tetrafluoromethane that is to be monitored in the direct fluorination reaction in the present embodiment, and thus the raw material organic compound is required to have two or more carbon atoms.

The raw material organic compound may be any type, and examples include aliphatic hydrocarbons such as hexane, heptane, and octane; alcohols such as ethanol, propanol, and butanol; ketones such as acetone; esters such as ethyl acetate and butyl acetate; low-molecular weight ethers such as diethyl ether and tetrahydrofuran; and polyethers typified by polyethylene glycol.

Examples of the raw material organic compound further include sulfides such as dimethyl sulfide; carboxylic acids such as acetic acid and adipic acid; halogenated alkyls such as 1,2-dichloroethane and 1,2,3,4-tetrachlorobutane; and aromatic compounds such as benzene, toluene, xylene, mesitylene, cymene, fluorene, carbazole, thiophene, pyrrole, furan, pyridine, triazine, benzophenone, salicylic acid, methyl salicylate, acetylsalicylic acid, methyl benzoate, benzoic acid, anisole, phenyl sulfide, and 1,2-dichlorobenzene.

The above-exemplified raw material organic compound may be substituted with various substituents, and such a substituted raw material organic compound can be used as the raw material organic compound in the method for producing a fluorine-containing organic compound pertaining to the present embodiment.

The fluorine-containing organic compound obtained by fluorination of a raw material organic compound may be any type and may be, for example, a fluorine-containing organic compound having a chemical structure in which some of the hydrogen atoms of a raw material organic compound are replaced with fluorine atoms or a fluorine-containing organic compound having a chemical structure in which all the hydrogen atoms of a raw material organic compound are replaced with fluorine atoms.

The fluorine gas used in the method for producing a fluorine-containing organic compound pertaining to the present embodiment may be a gas supplied from a gas cylinder or a gas generated by electrolysis of hydrogen fluoride on-site, for example. The fluorine gas may contain hydrogen fluoride.

As the material of the reaction container 11 used in the method for producing a fluorine-containing organic compound pertaining to the present embodiment, a material not undergoing vigorous reaction with fluorine gas is used. Examples of the material include stainless steels such as SUS316L and nickel copper alloys such as Monel (registered trademark).

Typically, the direct fluorination reaction in the embodiment can be performed at a temperature of −30° C. or more and 180° C. or less and a pressure of 0.01 MPa or more and 1.0 MPa or less. Tetrafluoromethane, which has a boiling point of about −128° C., is gas in reaction conditions of the direct fluorination reaction in the embodiment unless the reaction is performed at an excessively low temperature and high pressure, and does not stay in the reaction solution.

In the method for producing a fluorine-containing organic compound pertaining to the present embodiment, tetrafluoromethane is measured to monitor the occurrence of "burning" with fluorine gas. When "burning" is caused during reaction, tetrafluoromethane may be formed. The formed tetrafluoromethane then moves from the reaction solution to a gas phase 2 in the reaction container 11, and thus the gas phase 2 is analyzed to measure tetrafluoromethane.

The tetrafluoromethane contained in the gas phase 2 can be measured by any analyzer, and examples of the analyzer include an infrared spectrometer, a gas chromatograph, a liquid chromatograph, a nuclear magnetic resonance apparatus, and a mass spectrometer.

Of these analyzers, the infrared spectrometer is more preferred because tetrafluoromethane can be continuously measured when the gas phase 2 in the reaction container 11 is constantly introduced through a pipe or the like to a gas cell. For example, tetrafluoromethane can be measured at intervals of 0.1 seconds, 1 second, or several seconds.

To measure tetrafluoromethane by using an infrared spectrometer, peaks around wavelengths of 798 $cm^{-1}$, 1240 $cm^{-1}$, 1290 $cm^{-1}$, 1540 $cm^{-1}$, and 2200 $cm^{-1}$ can be monitored in the resulting chart, and monitored peaks are more preferably around wavelengths of 1240 $cm^{-1}$, 1290 $cm^{-1}$ and even more preferably around a wavelength of 1290 $cm^{-1}$. In such observation, there is no by-product having wavelengths interfering with the monitor of tetrafluoromethane, and thus abnormal "burning" can be certainly detected.

When tetrafluoromethane contained in the gas phase 2 is continuously measured with an infrared spectrometer, and, for example, a peak around a wavelength of 1290 cm$^{-1}$ has an intensity exceeding a predetermined intensity, the occurrence of side reactions including cutting of carbon-carbon bonds of the raw material organic compound is indicated, and thus the amount of the fluorine gas supplied to the reaction solution is reduced, or the supply of fluorine gas is stopped. For example, when a peak around a wavelength of 1290 cm$^{-1}$ has an intensity exceeding a predetermined intensity, a signal is automatically sent to a solenoid valve installed on the pipe for supplying fluorine gas, and the solenoid valve is automatically closed. With such a mechanism, the supply of fluorine gas to the reaction solution can be stopped immediately after the occurrence of a side reaction. For example, when the peak around a wavelength of 1290 cm$^{-1}$ has an intensity less than the predetermined intensity, the amount of fluorine gas supplied to the reaction solution can be increased, or the supply of fluorine gas can be started again.

The fluorine gas to be reacted with a raw material organic compound can be supplied into a reaction system by blowing fluorine gas through a pipe or the like into a raw material liquid in the reaction container 11. The fluorine gas may consist of only fluorine gas or may be a mixed gas in which fluorine gas is diluted with a dilution gas. As the dilution gas used for dilution, an inert gas such as nitrogen gas and argon can be used.

The apparatus for producing a fluorine-containing organic compound used in the present embodiment preferably has a structure capable of discharging the gas phase 2 from the reaction container 11. For example, an apparatus for producing a fluorine-containing organic compound having the following structure can be used: a reaction container 11 is tubular such that a raw material liquid flows from one end of the reaction container 11 toward the other end; the apparatus has a nozzle through which fluorine gas is blown from one end of the reaction container 11 into the reaction container 11; and a gas phase 2 can be discharged out of the reaction container 11. For example, an apparatus for producing a fluorine-containing organic compound having the following structure can also be used: the apparatus has a nozzle through which fluorine gas is blown from the bottom part of a reaction container 11 into the container; and a gas phase 2 can be discharged out of the reaction container 11.

When an apparatus for producing a fluorine-containing organic compound has such a structure as above, the gas phase 2 can be discharged from the reaction container 11, and accordingly a dilution gas or an excess fluorine gas is discharged from the reaction container 11. When "burning" is caused, tetrafluoromethane is discharged from the reaction container 11 together with the dilution gas or the excess fluorine gas. Measurement of the tetrafluoromethane in the discharged gas allows the apparatus for producing a fluorine-containing organic compound to have a simple structure.

The condition of the reaction between a raw material organic compound and fluorine gas is appropriately selected depending on the type of a raw material organic compound. In other words, depending on the type of a raw material organic compound, the reaction temperature, the reaction pressure, the concentration of fluorine gas in a mixed gas, the supply speed of fluorine gas, and the like are determined. These reaction conditions are preferably controlled such that "burning" is suppressed.

EXAMPLES

The present invention will next be described more specifically with reference to examples and comparative examples.

Example 1

First, the structure of an apparatus for producing a fluorine-containing organic compound will be described. The apparatus for producing a fluorine-containing organic compound has substantially the same structure as the apparatus for producing a fluorine-containing organic compound illustrated in FIG. 1 and includes a stainless steel reaction container having a capacity of 1 L. The reaction container is equipped with a stirrer having six flat turbines (in the production apparatus in FIG. 1, sign 31 indicates the stirrer), a fluorine gas introduction pipe, and a gas discharge pipe.

The fluorine gas introduction pipe is used to supply a fluorine gas diluted with nitrogen gas to the bottom part in the reaction container. The gas discharge pipe connects the upper part of the reaction container to a gas cell of an infrared spectrometer and is used to introduce the gas phase in the reaction container to the gas cell of the infrared spectrometer. At the upstream side of the gas discharge pipe from the infrared spectrometer, a regulator valve is provided to control the pressure in the reaction container.

Next, the method for producing a fluorine-containing organic compound by using the above apparatus for producing a fluorine-containing organic compound will be described with reference to a method of reacting fluorine gas with 1,2,3,4-tetrachlorobutane (hereinafter called "TCB") to give 1,2,3,4-tetrachloro-1,1,2,3,4,4-hexafluorobutane (hereinafter called "HFTCB") as an example.

In the reaction container, 60 g of TCB and 540 g of HFTCB were added and mixed to give a raw material liquid. In the example, TCB corresponds to the raw material organic compound, and HFTCB corresponds to the solvent. While the raw material liquid was stirred by using the stirrer at a rotation speed of 360 min$^{-1}$, fluorine gas was blown into the raw material liquid, and the reaction was performed. During the reaction, the gas phase in the reaction container was introduced into the gas cell of the infrared spectrometer, and the gas phase was continuously subjected to infrared spectroscopic analysis.

During the reaction, the temperature of the raw material liquid was set at 70° C., and the pressure in the reaction container was set at 0.45 MPa. The fluorine gas introduced into the reaction container was a mixed gas of nitrogen gas and fluorine gas, and the mixed gas had a fluorine gas concentration of 40% by volume. The flow rate of the mixed gas was 400 NmL/min (in terms of 0° C., 0.1 MPa).

Until about 5 minutes from the start of blowing of the mixed gas into the raw material liquid, the infrared spectroscopic analysis gave no unusual results. In other words, the infrared spectroscopic analysis gave a chart illustrated in FIG. 2A, in which a peak at a wavelength of 1290 cm$^{-1}$ was not observed (i.e., no tetrafluoromethane was detected).

From 5 minutes 20 seconds after the start of blowing of the mixed gas into the raw material liquid, the infrared spectroscopic analysis gave unusual results. In other words, the infrared spectroscopic analysis gave a chart illustrated in FIG. 2B, in which a peak at a wavelength of 1290 cm$^{-1}$ was observed (i.e., tetrafluoromethane was detected).

Hence, the supply of the mixed gas was stopped to immediately stop the reaction. While the reaction was stopped, the infrared spectroscopic analysis was continued.

Figure 2A:
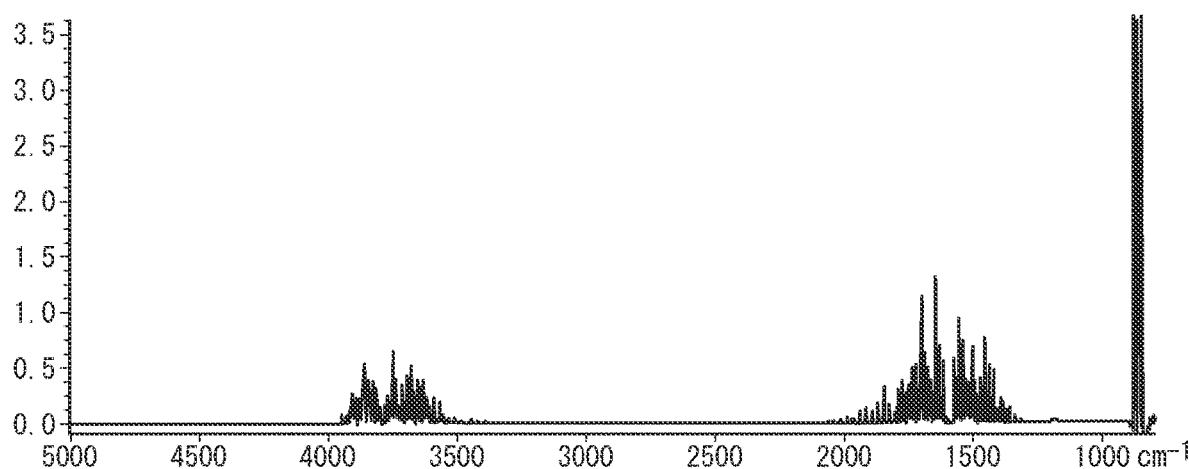
FIGS. 2A-2B are charts illustrating infrared spectroscopic analysis results of gas phases.
Figure 2B:
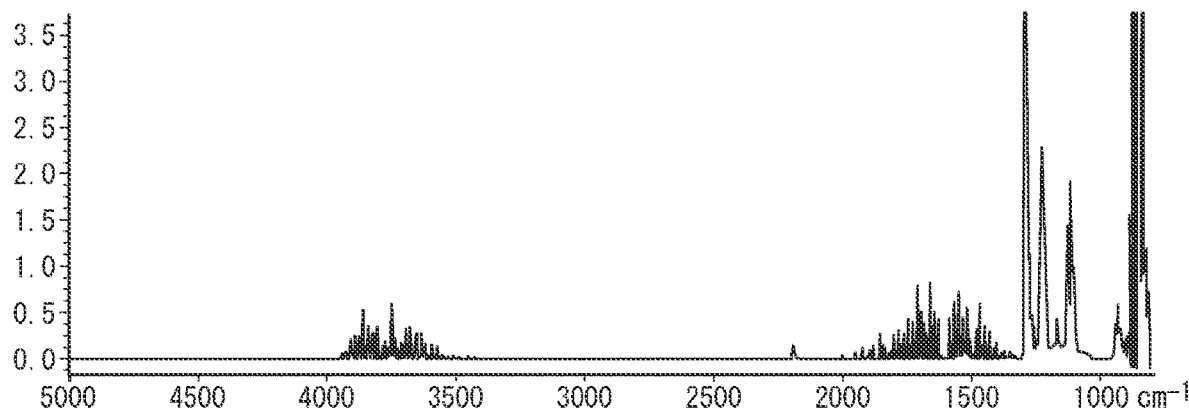

After observation that the infrared spectroscopic analysis gave a chart without unusual results illustrated in FIG. 2A, the mixed gas was supplied again to resume the reaction.

After that, the infrared spectroscopic analysis continued to give a chart without unusual results, thus the reaction was performed for 5 hours in total, and the reaction was stopped after the mixed gas flowed in a total volume of 48 L (in terms of 0° C., 0.1 MPa). Nitrogen gas was used to purge the reaction solution for a while to remove the gas dissolved in the reaction solution, and then the mass of the reaction solution was determined to give an increase of 30 g as compared with before the reaction. This indicated no loss of the reaction solution.

The obtained reaction solution was analyzed to identify and quantitatively determine compounds contained in the reaction solution. As a result, the reaction solution contained HFTCB, and the yield of the resulting HFTCB was 69% on the basis of TCB. The identification and the quantitative determination were performed in the following manner: The mass of the obtained reaction solution was determined, then a portion of the reaction solution was analyzed by gas chromatography to determine the HFTCB concentration (% by mass) in the reaction solution, and thus the identification and the quantitative determination were performed.

The yield of the HFTCB was calculated in accordance with the following equation.

Yield=(increase molar amount of HFTCB)/(initial molar amount of TCB)=(64.2 g/304)/(60.0 g/196)=0.69

Comparative Example 1

The reaction was performed in the same manner as in Example 1 except that an apparatus for producing a fluorine-containing organic compound included no infrared spectrometer, and the gas phase was not subjected to infrared spectroscopic analysis. The reaction continued for 5 hours without discontinuation of the supply of the mixed gas, and then the supply of the mixed gas was stopped to stop the reaction. Nitrogen gas was used to purge the reaction solution for a while to remove the gas dissolved in the reaction solution, and then the mass of the reaction solution was determined to give a decrease of 80 g as compared with before the reaction. This is supposed to be because TCB as the raw material organic compound or HFTCB used as the solvent underwent abnormal reactions with fluorine gas (for example, cutting of carbon-carbon bonds) to form low-boiling substances such as tetrafluoromethane.

This is thought to be a decrease in mass of the reaction solution because "burning" of TCB as the raw material organic compound with fluorine gas resulted in the formation of various fluorine compounds having 1 to 4 carbon atoms, and these fluorine compounds gasified and were removed from the reaction solution. It is thought that although abnormal reactions were caused from 5 minutes 20 seconds after the start of blowing of the mixed gas into the raw material liquid, the reaction continued, giving abnormal results.

Reference Example

The reaction was performed in the same manner as in Example 1 except that the pressure in the reaction container was 0.15 MPa, and the mixed gas had a fluorine gas concentration of 20% by volume. The reaction was performed for 10 hours, and the reaction was stopped after the mixed gas flowed in a total volume of 48 L (in terms of 0° C., 0.1 MPa). During the reaction, TCB and fluorine gas were normally reacted to give HFTCE as the target compound. In other words, during the reaction, the gas phase in the reaction container was introduced into the gas cell of the infrared spectrometer, and the gas phase was continuously subjected to infrared spectroscopic analysis, but the fluorine gas was supplied at a small flow rate, and thus a peak at a wavelength of 1290 cm$^{-1}$ was not observed (i.e., no tetrafluoromethane was detected). The yield of the resulting HFTCB was 70% on the basis of TCB.

Example 2

The method for producing a fluorine-containing organic compound by using an apparatus for producing a fluorine-containing organic compound substantially the same as in Example 1 will be described with reference to a fluorination method of reacting hexaethylene glycol ester with fluorine gas as an example.

In the reaction container, 5 g of hexaethylene glycol di-perfluorobenzene ester in which both ends of hexaethylene glycol were protected with ester and 1,200 g of HFTCB were added and mixed to give a raw material liquid. In the example, hexaethylene glycol di-perfluorobenzene ester corresponds to the raw material organic compound, and HFTCB corresponds to the solvent. The structural formula of hexaethylene glycol di-perfluorobenzene ester is as shown below.

[Chemical Formula 1]

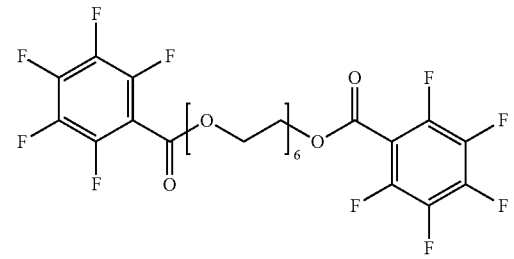

While the raw material liquid was stirred by using the stirrer at a rotation speed of 360 min$^{-1}$, fluorine gas was blown into the raw material liquid, and the reaction was performed. During the reaction, the gas phase in the reaction container was introduced into the gas cell of the infrared spectrometer, and the gas phase was continuously subjected to infrared spectroscopic analysis.

During the reaction, the temperature of the raw material liquid was set at 10° C., and the pressure in the reaction container was set at 0.2 MPa. The fluorine gas introduced into the reaction container was a mixed gas of nitrogen gas and fluorine gas, and the mixed gas had a fluorine gas concentration of 20% by volume. The flow rate of the mixed gas was 500 NmL/min (in terms of 0° C., 0.1 MPa).

From 8 minutes 30 seconds after the start of blowing of the mixed gas into the raw material liquid, the infrared spectroscopic analysis gave unusual results. In other words, as a result of the infrared spectroscopic analysis, a peak at a wavelength of 1290 cm$^{-1}$ was observed (i.e., tetrafluoromethane was detected). Hence, the supply of the mixed gas was stopped to immediately stop the reaction.

While the reaction was stopped, the infrared spectroscopic analysis was continued. After observation that the infrared spectroscopic analysis gave a chart without unusual results as with that illustrated in FIG. 2A, the mixed gas was supplied again to resume the reaction. After that, the infrared spectroscopic analysis continued to give a chart without unusual results, and thus the reaction was performed for 3 hours in total. Nitrogen gas was used to purge the reaction solution for a while to remove the gas dissolved in the reaction solution, and then the mass of the reaction solution was determined to give an increase of 4 g. This indicated no loss of the reaction solution.

The obtained reaction solution was analyzed to identify and quantitatively determine compounds contained in the reaction solution. As a result, the reaction solution contained a fluorinated compound of hexaethylene glycol di-perfluorobenzene ester, and the yield of the resulting fluorinated compound was 70% on the basis of hexaethylene glycol di-perfluorobenzene ester.

The yield of the resulting fluorinated compound was calculated in accordance with the following equation.

Yield=(increase molar amount of fluorinated compound of hexaethylene glycol di-perfluorobenzene ester)/(initial molar amount of hexaethylene glycol di-perfluorobenzene ester)=(6.8 g/1214.19)/(5.0 g/626.40)=0.70

The structural formula of the fluorinated compound of hexaethylene glycol di-perfluorobenzene ester (hexaethylene glycol di-perfluorocyclohexane ester) is as shown below.

[Chemical Formula 2]

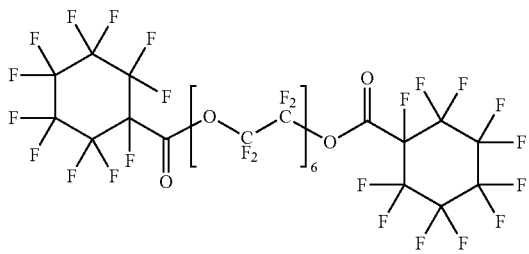

Comparative Example 2

The reaction was performed in the same manner as in Example 2 except that an apparatus for producing a fluorine-containing organic compound included no infrared spectrometer, and the gas phase was not subjected to infrared spectroscopic analysis. The reaction continued for 1 hour without discontinuation of the supply of the mixed gas, and then the supply of the mixed gas was stopped to stop the reaction. Nitrogen gas was used to purge the reaction solution for a while to remove the gas dissolved in the reaction solution, and then the mass of the reaction solution was determined to give a decrease of 17 g as compared with before the reaction. This is supposed to be because hexaethylene glycol di-perfluorobenzene ester as the raw material organic compound or HFTCB used as the solvent underwent abnormal reactions with fluorine gas (for example, cutting of carbon-carbon bonds) to form low-boiling substances such as tetrafluoromethane.

Example 3

The method for producing a fluorine-containing organic compound by using an apparatus for producing a fluorine-containing organic compound substantially the same as in Example 1 will be described with reference to a fluorination method of reacting 1,5-pentanedioic acid dimethyl ester with fluorine gas as an example.

In the reaction container, 10.30 g of 1,5-pentanedioic acid dimethyl ester and 900 g of HFTCB were added and mixed to give a raw material liquid. In the example, 1,5-pentanedioic acid dimethyl ester corresponds to the raw material organic compound, and HFTCB corresponds to the solvent.

While the raw material liquid was stirred by using the stirrer at a rotation speed of 370 $\text{min}^{-1}$, fluorine gas was blown into the raw material liquid, and the reaction was performed. During the reaction, the gas phase in the reaction container was introduced into the gas cell of the infrared spectrometer, and the gas phase was continuously subjected to infrared spectroscopic analysis.

During the reaction, the temperature of the raw material liquid was set at 0° C., and the pressure in the reaction container was set at 0.15 MPa. The fluorine gas introduced into the reaction container was a mixed gas of nitrogen gas and fluorine gas, and the mixed gas had a fluorine gas concentration of 20% by volume. The flow rate of the mixed gas was 300 NmL/min (in terms of 0° C., 0.1 MPa).

From 2 minutes after the start of blowing of the mixed gas into the raw material liquid, the infrared spectroscopic analysis gave unusual results. In other words, as a result of the infrared spectroscopic analysis, a peak at a wavelength of 1290 $\text{cm}^{-1}$ was observed (i.e., tetrafluoromethane was detected). Hence, the supply of the mixed gas was stopped to immediately stop the reaction.

While the reaction was stopped, the infrared spectroscopic analysis was continued. After observation that the infrared spectroscopic analysis gave a chart without unusual results illustrated in FIG. 2A, the mixed gas was supplied again to resume the reaction. After that, the infrared spectroscopic analysis continued to give a chart without unusual results, and thus the reaction was performed for 6 hours in total. Nitrogen gas was used to purge the reaction solution for a while to remove the gas dissolved in the reaction solution, and then the mass of the reaction solution was determined to give an increase of 10 g. This indicated no loss of the reaction solution.

The obtained reaction solution was analyzed to identify and quantitatively determine compounds contained in the reaction solution. As a result, the reaction solution contained a fluorinated compound of 1,5-pentanedioic acid dimethyl ester, and the yield of the resulting fluorinated compound was 75% on the basis of 1,5-pentanedioic acid dimethyl ester.

The yield of the resulting fluorinated compound was calculated in accordance with the following equation.

Yield=(increase molar amount of fluorinated compound of 1,5-pentanedioic acid dimethyl ester)/(initial molar amount of 1,5-pentanedioic acid dimethyl ester)=(18.14 g/376.05)/(10.30 g/160.17)=0.75

Comparative Example 3

The reaction was performed in the same manner as in Example 3 except that an apparatus for producing a fluorine-containing organic compound included no infrared spectrometer, and the gas phase was not subjected to infrared spectroscopic analysis. The reaction continued for 30 minutes without discontinuation of the supply of the mixed gas, and then the supply of the mixed gas was stopped to stop the reaction. Nitrogen gas was used to purge the reaction solution for a while to remove the gas dissolved in the reaction solution, and then the mass of the reaction solution was determined to give a decrease of 10 g as compared with before the reaction. This is supposed to be because 1,5-pentanedioic acid dimethyl ester as the raw material organic compound or HFTCB used as the solvent underwent abnormal reactions with fluorine gas (for example, cutting of carbon-carbon bonds) to form low-boiling substances such as tetrafluoromethane.

REFERENCE SIGNS LIST 1 material liquid
2 gas phase
11 reaction container
13 infrared spectrometer
31 stirrer

The invention claimed is:

1. A method for producing a fluorine-containing organic compound, the method comprising:
  reacting a raw material liquid containing a raw material organic compound having a hydrogen atom and two or more carbon atoms with fluorine gas in a reaction container to replace the hydrogen atom of the raw material organic compound with a fluorine atom to give the fluorine-containing organic compound,
  wherein tetrafluoromethane contained in a gas phase in the reaction container is continuously measured, and an amount of the fluorine gas supplied to the reaction container is controlled depending on a measured value of the tetrafluoromethane,
  wherein the raw material organic compound is 1,2,3,4-tetrachlorobutane, and the fluorine-containing organic compound is 1,2,3,4-tetrachloro-1,1,2,3,4,4-hexafluorobutane.

2. The method for producing the fluorine-containing organic compound according to claim 1, wherein the gas phase in the reaction container is introduced to an infrared spectrometer to measure the tetrafluoromethane.

3. The method for producing the fluorine-containing organic compound according to claim 2, wherein the infrared spectrometer is used to measure peaks around wavelengths of 798 $cm^{-1}$, 1240 $cm^{-1}$, 1290 $cm^{-1}$, 1540 $cm^{-1}$, and 2200 $cm^{-1}$.

4. The method for producing the fluorine-containing organic compound according to claim 2, wherein when the peak around a wavelength of 1290 $cm^{-1}$ measured with the infrared spectrometer has an intensity exceeding a predetermined intensity, the amount of the fluorine gas supplied is reduced, or the supply of the fluorine gas is stopped.

* * * * *